United States Patent

Hirai et al.

[11] Patent Number: 5,864,240
[45] Date of Patent: Jan. 26, 1999

[54] METHOD AND APPARATUS FOR MEASURING CONCENTRATION OF MATTER IN LIQUID BY USING MICROWAVES

[75] Inventors: Renzou Hirai, Tokyo; Shigeki Yamazu, Koshigaya, both of Japan

[73] Assignee: Kabushiki Kaisha Toshiba, Kawasaki, Japan

[21] Appl. No.: 790,425

[22] Filed: Jan. 29, 1997

[30] Foreign Application Priority Data

Jan. 31, 1996 [JP] Japan .................................. 8-016030

[51] Int. Cl.$^6$ .................................................. G01N 22/00
[52] U.S. Cl. .................. 324/639; 324/76.56; 324/76.77; 73/61.44
[58] Field of Search ..................................... 324/637, 639, 324/76.52, 76.55, 76.56, 76.59, 76.61, 76.77; 73/61.41, 61.43, 61.44

[56] References Cited

U.S. PATENT DOCUMENTS

| | | | |
|---|---|---|---|
| 4,486,714 | 12/1984 | Davis, Jr. et al. | 324/639 X |
| 4,764,718 | 8/1988 | Revus et al. | 324/640 |
| 4,767,982 | 8/1988 | Florig et al. | 324/640 |
| 5,006,785 | 4/1991 | Revus et al. | 324/639 |
| 5,793,216 | 8/1998 | Constant | 324/639 |

*Primary Examiner*—Glenn W. Brown
*Attorney, Agent, or Firm*—Oblon, Spivak, McClelland, Maier & Neustadt, P.C.

[57] ABSTRACT

An apparatus comprising a measuring unit for measuring a property of microwaves by transmitting microwaves through a fluid containing matter to be measured, a storing unit for storing a correction parameter set of a sensitivity coefficient and a mixture ratio concerning the matter to be measured, and a calculating unit for calculating a concentration of the matter to be measured from the property of the microwaves obtained by the measuring unit and the correction parameter set obtained in the storing unit.

10 Claims, 4 Drawing Sheets

| MATTER IN LIQUID TO BE MEASURED | PARAMETER SET (1SET) | | |
| --- | --- | --- | --- |
| | SENSITIVITY OF MATTER | MIXTURE RATIO | CONCENTRATION OF ADDITIVE IN PULP |
| ONLY PULP | (1.0) | ---- | (xp) |
| ADDITIVE A | a | A | $x_a$ |
| ADDITIVE B | b | B | $x_b$ |
| ADDITIVE C | c | C | $x_c$ |
| ADDITIVE D | d | D | $x_d$ |
| ADDITIVE E | e | E | $x_e$ |

F I G. 5

METHOD AND APPARATUS FOR MEASURING CONCENTRATION OF MATTER IN LIQUID BY USING MICROWAVES

BACKGROUND OF THE INVENTION

The present invention relates to a method and apparatus for measuring by using microwaves the concentration of dissolving matter, such as pulp suspension liquid, in which suspended matter (e.g., pulp) and/or an additive is dissolved.

When microwaves are incident on water, the microwaves have a phase lag ($\theta_1$) behind that in the case where microwaves are incident on a vacuum (air). When microwaves are incident on a suspension, such as sludge or pulp liquid, a greater phase lag ($\theta_2$) results.

This phenomenon is represented by the following equation:

$$\text{Concentration } X = C \cdot a_k \cdot \Delta\theta = C \cdot a_k \cdot (\theta_2 - \theta_1) \tag{1}$$

where C: a correction coefficient, $a_k$: a sensitivity coefficient, $\theta_1$: a phase lag in a case where microwaves are incident on reference liquid, and $\theta_2$: a phase lag in a case where microwaves are incident on suspension liquid.

The difference between the phase lags (phase difference: $\theta_2 - \theta_1$) is proportional to the sum of the concentration of suspended matter and the concentration of dissolved matter.

In recent years, concentration meters based on the above principle have been developed, and disclosed in Jpn. Pat. Appln. KOKAI Publications Nos. 4-238246 and 5-322801. The developed or disclosed concentration meters have many advantages, one of which is little influence of adhesion of suspended matter or bubbles in the liquid.

As regards pulp suspension liquid used in papermaker plants, a plurality of additives are added to produce each product (paper) in a constant mixture ratio. Assume that a pulp concentration (concentration of pulp as suspended matter) or additive concentration (concentration of an additive as dissolved matter) is measured by means of the concentration meter based on the aforementioned principle. When the concentrations of the additives (additives A and B) are individually measured, the indication of the concentration meter is proportional to the concentration, as shown in the equation (1) and FIG. 1. FIG. 1 is a diagram showing a result of measurement of individually measuring the pulp concentration and additive concentrations by a microwave concentration meter.

Since pulp and the additives A and B are different in physical properties, the sensitivity $a_k$ in the equation (1) is different between the additives. If the additives are mixed, the sensitivity of the mixture cannot be necessarily expected accurately, so that an error may arise in the measured concentration value depending on the mixture ratio. Further, in the case of the concentration meter based on the above principle, it is necessary to obtain in advance a reference phase lag ($\theta_1$) using reference liquid, for example, service water, which has a concentration of substantially zero. This operation is called zero adjustment or zero-point adjustment.

To execute such a zero adjustment operation, it is necessary that a piping system including the concentration meter have a structure as shown in FIGS. 2A and 2B. Referring to FIGS. 2A and 2B, to perform zero adjustment, a stop valve 52 on the side of a bypass pipe 51 is first opened to allow pulp suspension to pass through the bypass pipe, and then, stop valves 53, 54 on the side of a main pipe 55 are closed. Thereafter, the portion of the main pipe between the stop valves 53 and 54 is filled with reference liquid through a supply port 57. Thus, the zero adjustment of the concentration meter 56 is completed.

As described above, in the conventional concentration meter using microwaves, the measured concentration value may involve an error depending on the mixture ratio of the additives added to the pulp suspension. Moreover, to perform zero-point adjustment, the concentration meter must comprise a bypass pipe and stop valves, and an operation using them are required to fill the concentration meter with reference liquid.

BRIEF SUMMARY OF THE INVENTION

An object of the present invention is to provide a method and apparatus for accurately and easily measuring the concentration of matter in liquid by using microwaves, and more specifically to provide a method and apparatus for accurately and easily measuring the concentration of suspended matter and/or dissolved matter in suspension by using microwaves.

The above object is achieved by a method comprising: a measuring step for measuring a property of microwaves by transmitting microwaves through a fluid containing matter to be measured; a storing step for storing a correction parameter set of a sensitivity coefficient and a mixture ratio concerning the matter to be measured; and a calculating step for calculating a concentration of the matter to be measured from the property of the microwaves obtained in the measuring step and the correction parameter set obtained in the storing step.

The above object is achieved by an apparatus comprising: measuring means for measuring a property of microwaves by transmitting microwaves through a fluid containing matter to be measured; storing means for storing a correction parameter set of a sensitivity coefficient and a mixture ratio concerning the matter to be measured; and calculating means for calculating a concentration of the matter to be measured from the property of the microwaves obtained by the measuring means and the correction parameter set obtained in the storing means.

According to the present invention, microwaves are transmitted through a fluid containing matter to be measured and a property of the microwaves is measured, thereby obtaining the concentration of the matter in the fluid. In other words, if the fluid contains only one kind of matter, the property of the transmitted microwaves has a specific relationship to the matter in connection with the concentration and the sensitivity coefficient of the matter. The concentration of the matter is thus obtained utilizing the relationship.

The storing means store, as correction parameter sets, the sensitivity coefficients and the mixture ratios of the respective kinds of matter in a mix additive containing a plurality of kinds of matter of different sensitivity coefficients with respect to the property of the microwaves. The calculating means calculate the concentration of at least matter to be measured, based on the information including the property of the microwaves and the correction parameter set. Therefore, even if an additive is mixed in the fluid to be measured, if the sensitivity coefficients and the mixture ratios of the respective kinds of matter are known in advance, a value corresponding to the sensitivity coefficient of the mixture can be obtained. Thus, the concentration of the matter to be measured can be calculated.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 2A and 2B are diagrams showing a piping system including a conventional concentration meter, in which FIG. 2A is a plan view and FIG. 2B is a front view;

FIG. 5 is a diagram showing an example of data groups of the sensitivities and mixture ratios of additives used in the embodiment.

DETAILED DESCRIPTION OF THE INVENTION

A preferred embodiment of the present invention will now be described.

Figure 1:
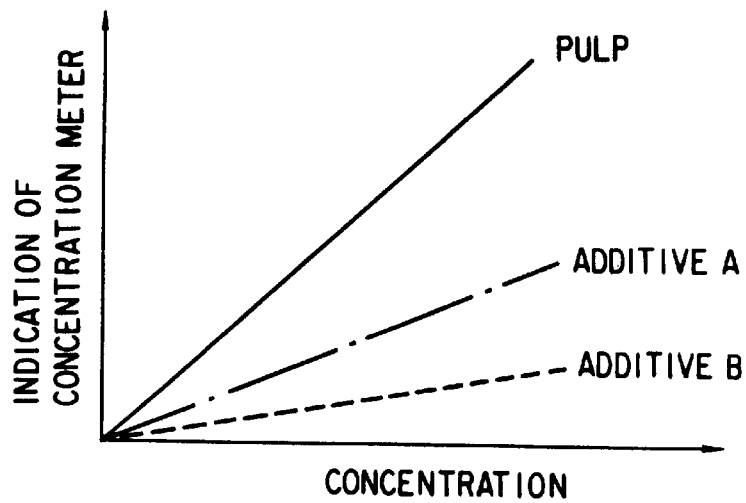
FIG. 1 is a diagram showing results of measurement in which the pulp concentration and additive concentrations are individually measured by a microwave concentration meter.
Figure 2A:
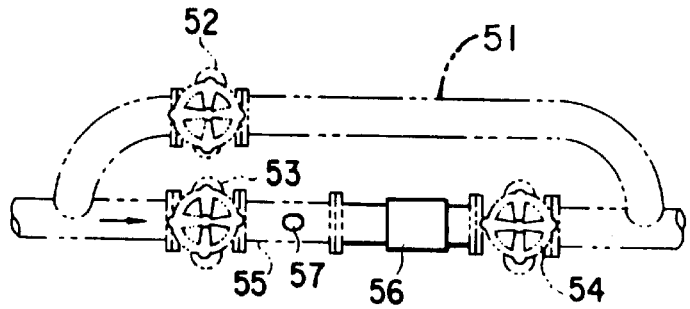
Figure 2B:
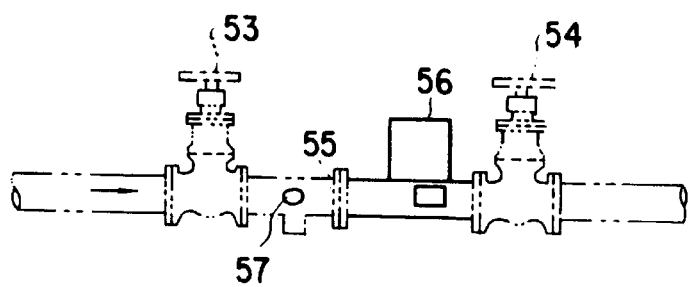
Figure 3:
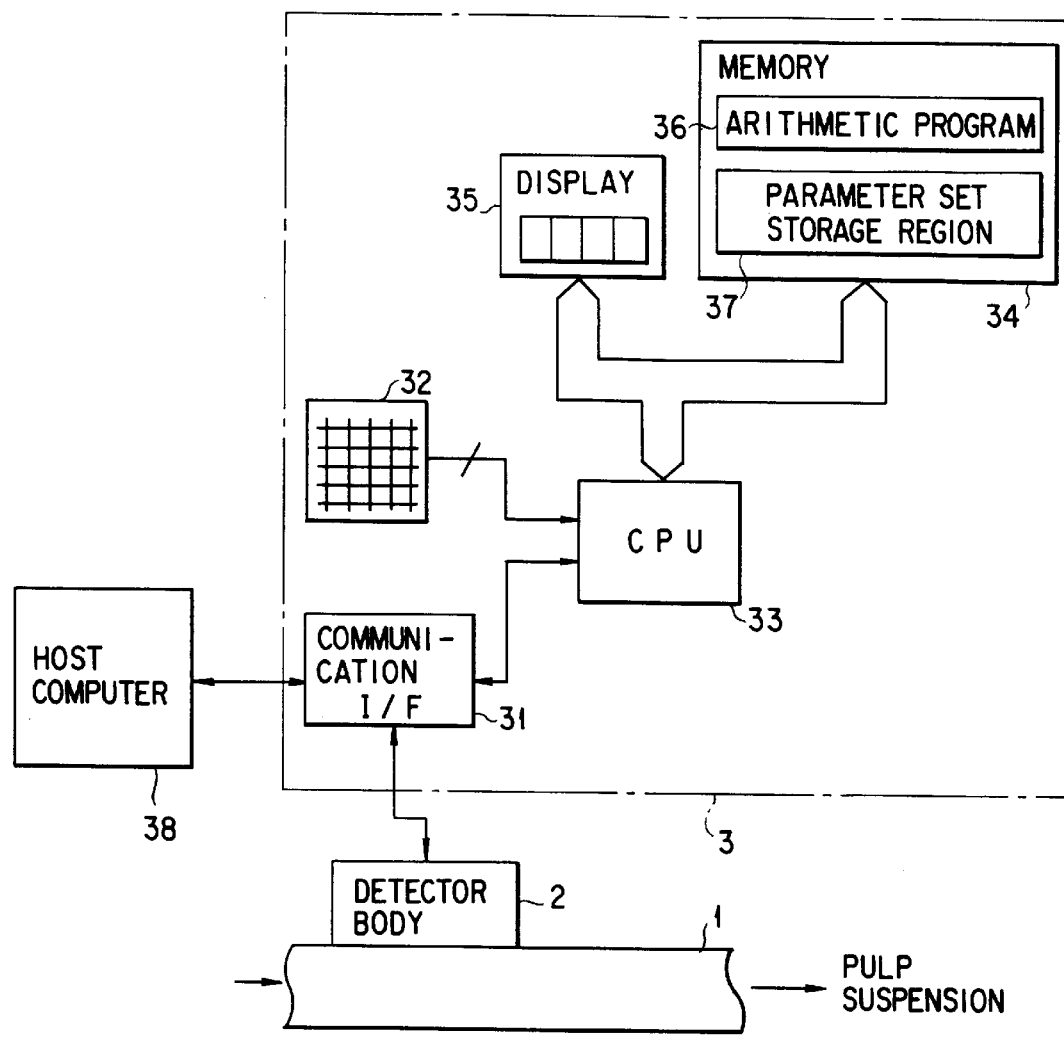
FIG. 3 is a diagram showing an embodiment of a concentration meter using microwaves according to the present invention.

A concentration meter of the present invention, i.e., an apparatus for measuring the concentration of dissolved matter and/or suspended matter in liquid, measures the concentration of matter in, for example, pulp liquid flowing through a pipeline. As shown in FIG. 3, a concentration meter according to a preferred embodiment of the present invention comprises a detector body 2 and a calculation display unit 3. The calculation display unit 3 is connected to a host computer 38 by a wire or radio, if necessary. The host computer 38 supplies instructions to the apparatus of the present invention and receives data therefrom. The detector body 2 and the calculation display unit 3 are connected by suitable connecting means so as to achieve data transmission and reception.

The detector body 2 is fixed to a pipeline 1, while the calculation display unit 3 may be arranged either in proximity to or apart from the detector body 2. The concentration meter of the present invention may be comprised of one calculation display unit 3 and a plurality of detector bodies 2. In this case, the one calculation display unit 3 is capable of processing data supplied from the respective detector bodies 2. For this purpose, the calculation display unit 3 should have an arithmetic processing system which a person skilled in the art usually employs: for example, an arithmetic processing system using a multiple CPU, or a processing system for processing data from the individual detector bodies in a time-dividing manner.

Figure 4:
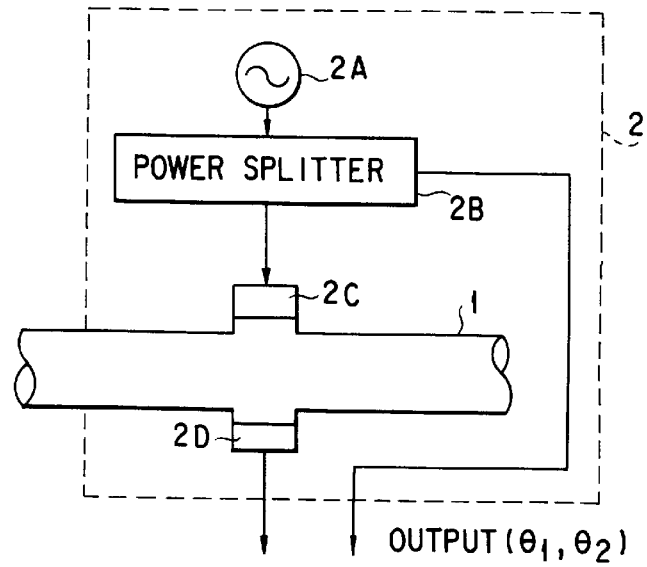
FIG. 4 is a diagram showing details of the detector body shown in FIG. 3.

As shown in FIG. 4, the detector body 2 comprises a microwave oscillator 2A, a power splitter 2B, a transmission antenna 2C and a reception antenna 2D. Microwaves are input to pulp suspension flowing through the pipeline 1, and signals (from the power splitter 2B and the reception antenna 2D) are output from the detector body 2. Using the phase lags, the concentration can be calculated from the equation (1) by the calculation display unit 3.

The calculation display unit 3 comprises a communication interface 31 for receiving a measurement result obtained by the detector body 2, a key board 32 for inputting data, a CPU 33, a memory 34 and a display 35. The CPU 33 operates in accordance with an arithmetic program 36 stored in the memory 34. It calculates a concentration of, for example, pulp or an additive flowing through the pipeline 1, using the measurement result supplied from the detector body 2 and a correction parameter set stored in a parameter set storage region 37, and causes the display 35 to display the concentration. The memory 34 includes the arithmetic program 36 and the parameter set storage region 37. The parameter set storage region 37 stores a correction parameter set as shown in FIG. 5. A set of correction parameters includes information on the mixture ratio of each additive to the liquid used for producing a product or a step of producing the product and the sensitivity of matter (additive or pulp) contained in the liquid. The correction parameter sets are obtained by utilizing the fact that liquid containing a plurality of additives mixed in a specific ratio in accordance with a product or a step for producing a product is mixed at least as a result in pulp suspension in a paper-maker plant. Since the kind of the additives in the liquid and the mixture ratio vary depending on the product or the producing step, the number of correction parameter sets corresponds to the number of kinds of pulp suspensions which are caused to flow through the pipeline 1. In accordance with the kind of pulp suspension flowing through the pipeline 1, the arithmetic program 36 switches the correction parameter set which the CPU 33 uses to calculate the concentration. The keyboard 32 is used to input various data and the contents of the correction parameter set. The display 35 displays calculated concentrations of the pulp suspension liquid.

The sensitivity in the concentration meter for each additive and the ratio of the additive to a pulp suspension liquid are known in advance through preparatory measurement or the like, for example as shown in FIG. 5. In other words, FIG. 5 shows an example of a mixed additive consisting of a plurality of kinds of matter contained in the liquid to be measured.

FIG. 5 is a diagram showing an example of the correction parameter set of the sensitivities and mixture ratios of additives used in the concentration measurement method in the concentration meter according to the embodiment of the present invention.

In FIG. 5, a symbol "a" denotes the sensitivity of an additive A, which is different from "a" in the equation (1).

Assuming that the mass of the pulp is $W_p$ and the mass of water is $W_w$, the pulp concentration x is obtained by the following equation:

$$x = W_p/(W_p + W_w) \quad (2)$$

The equation (2) is simply obtained by the definition of the concentration.

When the additive A is added to the pulp in a ratio A, the indication value of the apparent concentration is obtained by the following equation:

$$x_a = a \cdot A \cdot x \quad (3)$$

The indication values of the apparent concentrations of the other additives are obtained in the same manner as follows:

$$x_b = b \cdot B \cdot x \quad (4)$$

$$x_c = c \cdot C \cdot x \quad (5)$$

$$x_d = d \cdot D \cdot x \quad (6)$$

$$x_e = e \cdot E \cdot x \quad (7)$$

Therefore, when the pulp and the all additives are mixed, the indication value M of the apparent concentration of the concentration meter is obtained by adding all the above equations (2) to (7).

$$M = x + x_a + x_b + x_c + x_d + x_e = x(1 + a \cdot A + b \cdot B + c \cdot C + d \cdot D + e \cdot E) \quad (8)$$

Therefore, the pulp concentration x is obtained by the following equation:

$$x = M/(1 + a \cdot A + b \cdot B + c \cdot C + d \cdot D + e \cdot E) \quad (9)$$

On the other hand, the concentration X of all solid components including the additives (concentration of the suspended matter and the dissolving matter) is obtained as follows from the equation (9) and the mixture ratios of the additives shown in FIG. 5:

$$\begin{aligned} X &= x + A \cdot x + B \cdot x + C \cdot x + D \cdot x + E \cdot x \\ &= x(1 + A + B + C + D + E) \\ &= \{M(1 + A + B + C + D + E)\}/ \\ &\quad (1 + a \cdot A + b \cdot B + c \cdot C + d \cdot D + e \cdot E) \\ &= k \cdot M \end{aligned} \quad (10)$$

where $$k = (1 + A + B + C + D + E)/(1 + a \cdot A + b \cdot B + c \cdot C + d \cdot D + e \cdot E) \quad (11)$$

On the other hand, the indication value of the apparent concentration of the concentration meter is obtained by the equation (1) as $M = C \cdot a_k \cdot \Delta\theta$, which is substituted in the equation (10).

$$X = k \cdot C \cdot a_k \cdot \Delta\theta = k \cdot C \cdot a_k(\theta_1 - \theta_2) \quad (12)$$

In this equation, $a_k$ is not the sensitivity of the additive A but the general sensitivity coefficient as in the equation (1).

Based on the above, a reference phase angle $\theta_1$ is obtained by the following equation:

$$\theta_1 = \theta_2 - X/(k \cdot C \cdot a_k) \quad (13)$$

The concentration meter is operated during a manufacturing process using a pulp suspension to measure a phase angle $\theta_2$ when microwaves are incident on the suspension. At the same time, a sample of the pulp suspension to be measured by the concentration meter is extracted from the plant, and the concentration X of all solid components is measured by manual analysis.

As the manual analysis, it is possible to employ a method of drying and solidifying the extracted sample and obtaining the difference in mass between the sample and the solidified sample, thereby calculating the concentration X of all the solid components.

When an object to be measure is not specified, general values are used for the correction coefficient C and the sensitivity coefficient $a_k$. As a practical example, a value determined by the diameter of the pipe line is input as the sensitivity coefficient $a_k$, and "1" is input as the correction coefficient C, if correction is not particularly required.

All the values of the right side of the equation (13) are determined by the above calculations, so that the reference phase angle $\theta_1$ can be obtained. Thus, it is unnecessary to fill the pipeline with the reference liquid to perform the zero adjustment.

Using the indication value M of the apparent concentration obtained by the concentration meter, the pulp concentration x can be calculated from the equation (9).

Further, the concentration $x_a$ of the additive A is obtained as follows by substituting the equation (9) in the equation (3) to obtain $x_a$.

$$X_a = (a \cdot A \cdot M)/(1 + a \cdot A + b \cdot B + c \cdot C + d \cdot D + e \cdot E) \quad (14)$$

Thus, the concentration of a single additive can also be calculated. The concentrations $x_b$ to $x_e$ of the additives A to E can be obtained in the same manner as described above.

Figure 6:
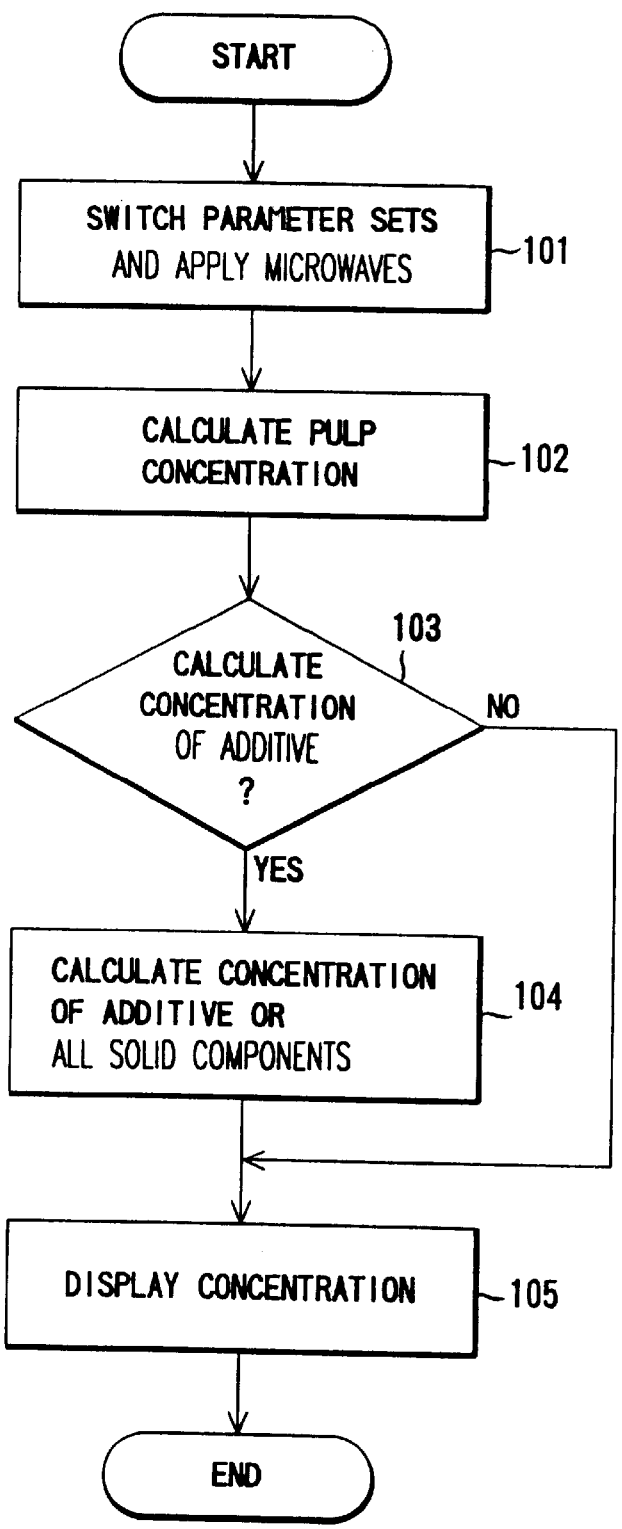
FIG. 6 is a flowchart showing a concentration measuring method according to the embodiment of the present invention.

An operation of the aforementioned concentration meter according to the embodiment of the present invention will now be described with reference to FIG. 6. First, a concentration measurement operation of the concentration meter, which has been subjected to zero-adjustment, will be described. In Step 101, the correction parameter sets are switched in accordance with the kind of the pulp suspension flowing through the pipeline 1 based on communication information supplied through the communication interface 31 from the host computer which monitors and controls the overall plants, information stored in the memory 34 concerning a preset production schedule for a product, or information input through the keyboard 32.

Next, in Step 101, microwaves are applied to the pulp suspension flowing through the pipeline 1, and the phase lag $\theta_2$ is obtained.

In Step 102, the CPU 33 substitutes the phase difference obtained by the above step in the equation (1) to obtain the indication value M of the apparent concentration in the concentration meter. Further, the indication value M of the apparent concentration of the concentration meter and the contents of the correction parameter sets are substituted in the equation (9), thereby calculating the pulp concentration x.

In Steps 103 and 104, if it is requested that the concentration (e.g., $x_a$) of an additive be obtained, the concentration $x_a$ is calculated from the equation (14). If it is requested that the concentration X of all solid components be obtained, the concentration X is calculated from the equation (10).

In Step 105, the pulp concentration x, the concentration (e.g., $x_a$) of the additive, if requested, and the concentration X of all solid components are displayed by the display 35.

A zero-adjustment operation will now be described.

First, microwaves are applied to the pulp suspension which flows through the pipeline 1 and corresponds to a correction parameter set, and the phase lag $\theta_2$ is measured.

At the same time, a sample is extracted from the pulp suspension from which the phase lag $\theta_2$ is measured. Then, the concentration X of the solid components of the suspension is obtained by means of the absolute dry method.

Subsequently, the phase lag $\theta_2$, the concentration X of the solid components and the values of the correction parameter set are substituted in the equation (13), thereby obtaining a reference phase angle $\theta_1$.

As described above, according to the concentration meter and the concentration measuring method of the embodiment of the present invention, the correction parameter sets are prepared in advance, and the pulp concentration x, the concentration (e.g., $x_a$) of an additive or the concentration X of all solid components is calculated from the equation (9), (14) or (10) on the basis of the measurement result obtained by the detector body 2 and the parameter sets. Therefore, even if a mixed additive has been added to the pulp suspension, the concentration of the pulp or all solid components (the sum of the pulp and additive concentrations) in the suspension can be accurately measured in consideration of the influence of the mixture.

Further, the pulp concentration of the pulp suspension during a manufacturing process is measured by manual analysis, while the concentration X of all solid components is measured by the concentration meter, so that the reference phase angle $\theta_1$ can be obtained. Thus, the zero adjustment using reference liquid is not required.

Therefore, a bypass pipe for zero-point adjustment, stop valves for filling the concentration meter with the reference liquid and an operation using them are not required.

As regards the preset correction parameter sets, a set of sensitivities and the mixture ratios of additives is determined for each of the products, as shown in FIG. 5. According to the embodiment, as described before, a plurality of correction parameters are stored in the memory, in such a manner that a correction parameter set can be selected for every product. Therefore, data can be easily switched for the respective products. Further, as described before, a parameter can be selected by an input through the keyboard or by an external communication signal.

As has been described above in detail, the present invention provides a concentration meter by which the concentration of pulp in pulp suspension can be accurately measured, even if the pulp suspension contains an additive. The present invention also provides a concentration meter by which the concentrations of additives in pulp suspension can be accurately measured. Moreover, the present invention provides a concentration meter which does not require a bypass pipeline for the zero-point adjustment or an operation for filling the concentration meter with reference liquid.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

We claim:

1. A method comprising:

a measuring step for measuring a property of microwaves by transmitting microwaves through a fluid containing a plurality of kinds of matter to be measured;

a storing step for storing correction parameter sets, each set being defined by a mixture ratio of the kind of matter to be measured and a sensitivity coefficient in the mixture ratio; and a calculating step for calculating concentrations of the plurality of kinds of matter to be measured from the property of the microwaves obtained in the measuring step and the correction parameter sets obtained in the storing step.

2. The method according to claim 1, wherein the calculating step includes a step of measuring a concentration of at least one of suspended matter and dissolved matter in the fluid.

3. An apparatus comprising:

measuring means for measuring a property of microwaves by transmitting microwaves through a fluid containing a plurality of kinds of matter to be measured;

storing means for storing correction parameter sets, each set being defined by a mixture ratio of the kind of matter to be measured and a sensitivity coefficient in the mixture ratio; and calculating means for calculating concentrations of the plurality of kinds of matter to be measured from the property of the microwaves obtained by the measuring means and the correction parameter sets obtained from the storing means.

4. The apparatus according to claim 3, wherein the storing means include means for storing correction parameter sets, each set corresponding to at least one of suspended matter and dissolved matter in the fluid.

5. The apparatus according to claim 3, wherein:

the storing means include means for storing a plurality of correction parameter sets respectively corresponding to a plurality of kinds of matter to be measured; and the calculating means include switching means for switching the correction parameter sets to be used in calculation in accordance with the kinds of matter to be measured.

6. The apparatus according to claim 3, wherein the calculating means include means for obtaining a reference point of the property of the microwaves, based on the property of the microwaves with respect to the matter to be measured and the concentration of the matter.

7. The apparatus according to claim 3, wherein:

a result of measuring the property of the microwaves is a first phase lag in transmitting the microwaves in the fluid;

a reference point of the property of the microwaves is a second phase lag in transmitting the microwaves in fluid which substantially does not contain matter to be measured; and the property of the microwave is a difference between the first and second phase lags.

8. The apparatus according to claim 3, further comprising control means for controlling the measuring means.

9. The apparatus according to claim 8, wherein the control means include means for controlling a measuring operation of the measuring means, based on instructions from a host computer.

10. The apparatus according to claim 8, further comprising a timer for initiating a measuring operation of the measuring means in a time dividing manner.

* * * * *